United States Patent [19]

Kita et al.

[11] Patent Number: 4,954,514
[45] Date of Patent: Sep. 4, 1990

[54] (DI-TERT-BUTYLHYDROXYPHENYL)THIO DERIVATIVES AND ANTIARTERIOSCHLEROSIS COMPOSITIONS THEREOF

[75] Inventors: Toru Kita; Shuh Narumiya, Kyoto; Masayuki Narisada, Osaka; Fumihio Watanabe, Nara; Masami Doteuchi, Owaka; Takuji Mizui, Hygo all of Japan

[73] Assignee: Shionogi & Co, Ltd, Owaka, Japan

[21] Appl. No.: 451,743

[22] Filed: Dec. 18, 1989

[30] Foreign Application Priority Data

Jan. 25, 1989 [JP] Japan .................................. 1-15387

[51] Int. Cl.$^5$ ................... C07D 257/04; A61K 31/41; A61K 31/05; C07C 147/00
[52] U.S. Cl. .................................... 514/381; 514/519; 548/252; 558/396; 564/162
[58] Field of Search ................ 548/252; 514/381, 618, 514/519; 564/162; 558/396

[56] References Cited

U.S. PATENT DOCUMENTS

| | | | |
|---|---|---|---|
| 3,337,576 | 8/1967 | Buchanan | 558/396 |
| 4,029,812 | 6/1977 | Wagner et al. | 424/324 |
| 4,076,841 | 2/1978 | Wagner et al. | 424/324 |
| 4,755,524 | 7/1988 | Mueller et al. | 548/252 |

FOREIGN PATENT DOCUMENTS 0190682  8/1986  European Pat. Off. .
1936463  4/1971  Fed. Rep. of Germany .
2406812  8/1974  Fed. Rep. of Germany .

OTHER PUBLICATIONS

Chemical Abstracts, vol. 94, No. 5, Feb. 2, 1981, Columbus, Oh., USA.
Mamedov, CH.I., "Synthesis of sulfur-containing derivatives of 2,6-di-tert-butylphenols", p. 528, abstract-No. 94:30 290c & Mater. Nauchn. Konf. Aspir. Akad. Nauk. Az. SSR 1980, 1, 127-131.

Primary Examiner—David B. Springer
Attorney, Agent, or Firm—Wenderoth, Lind & Ponack

[57] ABSTRACT

(Di-tert-butylhydroxyphenyl)thio derivatives of the formula:

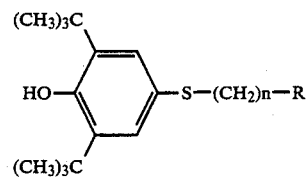

wherein R is cyano, carbamoyl, or 5-tetrazolyl; n is an integer of 2 to 6; provided that when R is cyano, n is not 2; or a pharmaceutically acceptable salt thereof; useful in treating arteriosclerosis, ulcer, inflammation, allergy, or the like.

2 Claims, No Drawings

(DI-TERT-BUTYLHYDROXYPHENYL)THIO DERIVATIVES AND ANTIARTERIOSCHLEROSIS COMPOSITIONS THEREOF

BACKGROUND OF THE INVENTION

1. Field of the Invention

This invention relates to di-tert-butylhydroxyphenylthio derivatives which may be useful as medicine. More particularly, it relates to those intramolecularly having residues derived from saturated aliphatic acid, which inhibit the incorporation of LDL (Low Density Lipoprotein) by preventing the denaturation of LDL and are therefore useful as an anti-arteriosclerosis agent.

Beside, they have preventive activity to oxidation of lipid, ulcer formation, and lipoxygenase inhibitory actions based on their anti-oxidation activities and may be therefore useful as agent for vessel disorder, anti-ulcer agent, anti-inflammatory agent, anti-allergy agent, and the like.

2. Description of the Prior Art

Atherosclerosis is thought to occur in an initial but significant stage of arteriosclerosis, in such a manner that lipoid material mainly consisting cholesterol moves into the arterial wall to form foam cells accompanied by hyperplasia and consequent sclerosis. Atherosclerosis has been thought not to occur due to a single factor but accumulated factors over a long period of time, such as hypertension, hyperlipemia, excessive cigarette smoking, obesity, diabetes mellitus, hyperuricemia, stress, heredity, lack of exercise, etc. Among those factors, the behavior of cholesterol existing as LDL in blood is noted. What is especially important are penetration of LDL into the arterial wall and the incorporation of LDL into macrophages, and the subsequent accumulation of cholesterol at the wall and the vessel disorder. On the other hand, the following factors are considered to promote the occurrence of atherosclerosis: the increase of blood cholesterol due to the troubles on the incorporation of LDL into liver and the metabolism of LDL in liver, the hydrodynamic state of blood due to the change in the physical properties of red blood cell, etc., the damage of endothelium, the abnormal hyperplasia of the arterial wall and the depression of the lipid utilization in arterial tissues, and the like.

For the drug therapy of atherosclerosis, there have heretofore been used anti-arteriosclerosis agents such as pyridinol carbamate; lipid lowering agents such as chlofibrate, nicotinic acid, alpha-tyroxine and chloestyramine; and anti-platelet agents such as dipyridamole and aspirin, etc. Also, di-tert-butylphenol derivatives having anti-arteriosclerosis activity are disclosed in JP. Publication Nos. 77-27144, 85-39362, 77-125171, or the like. Further, structurally related compounds having anti-oxidative activity are disclosed in JP. Unexam. Publication Nos. 74-75551, 74-75552, 83-90545, 86-191670, 86-197554, 86-210073, 86-218570, 86-268664, 88-310820, 88-310821, U.S. Pat. No. 4,076,841 and Chemical Abstract (C.A.) Vol. 94, 30290c, 1981 and the like.

It is generally considered that normal LDL are not incorporated by reticuloenthelial cells (scavenger cells) such as macrophages and kupffer cells, but denaturated LDL are incorporated through a receptor thereto. Also, it is considered that even when a large amount of cholesterol is accumulated in cells, the receptor for denaturated LDL does not decrease in number in cells, so that the accumulation of cholesterol is unlimitedly enhanced whereby the conversion of reticuloenthelial cells into foam may take place resulting in establishment of arteriosclerosis.

According to the above consideration, atherosclerosis may be prevented by inhibiting the production of denatured LDL. Development of drugs which can inhibit the production of denatured LDL has thus been desired, but satisfaction is presently not obtained in this respect.

SUMMARY (Di-tert-Butylhydroxyphenyl)thio derivatives of the formula:

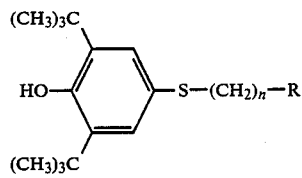

wherein R is cyano, carbamoyl, or 5-tetrazolyl; n indicates an integer of from 2 to 6; provided that when R is cyano, n does not indicate 2 or a pharmaceutically acceptable salt thereof.

Said compounds which inhibit LDL from being incorporated by macrophages and oxidizing fatty acids are useful in treating arteriosclerosis, ulcer, inflammation, or allergy.

DESCRIPTION OF THE PREFERRED EMBODIMENTS

As the result of an extensive study, the present invention provided compounds of the following formula:

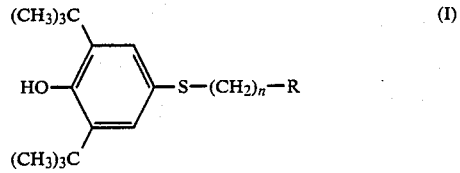

wherein R is cyano, carbamoyl, or 5-tetrazolyl; n indicates an integer of from 2 to 6, provided that when R is cyano, n does not indicate 2; and pharmaceutically acceptable salts thereof, and completed this invention.

In the formula (I), the alkylene represented by "$-(CH_2)n-$" includes ethylene, trimethylene, tetramethylene, pentamethylene, hexamethylene. When R is cyano, preferably n is 3 to 6.

When R is carbamoyl, n is preferably an integer of from 2 to 6 and especially 5. When R is 5-tetrazolyl, preferably n is an integer of from 2 to 6.

In this specification, 5-tetrazolyl means 5-1H-tetrazolyl or 5-2H-tetrazolyl or their mixture.

Salts of the compound of formula (I) when R is free tetrazolyl represents salts with alkali metal (e.g., lithium, sodium, potassium, or the like), with alkaline earth metal (e.g., calcium, magnesium, or the like), with organic base (e.g., triethylamine, 2-aminobutane, tert-butylamine, diisopropylethylamine, n-butylmethylamine, n-butyldimethylamine, tri-n-butylamine, dicyclohexylamine, N-isopropylcyclohexylamine, furfurylamine, benzylamine, methylbenzylamine dibenzylamine N,N-dimethylbenzylamine, 2-chlorobenzylamine, 4- methoxybenzylamine, 1-napthylmethylamine, diphenylbenzylamine, triphenylamine, 1-napthylamine, 1-aminoanthracene, 2-aminoantracene, dehyroabiethylamine, N-methylmorpholine, pyridine, or the like), with amino acid (e.g., lysine, arginine, histidine, or the like), or the like. The compounds of this invention can be prepared as shown below.

The compounds (I) of this invention are prepared by reacting 2,6-di-tert-butyl-4-mercaptophenol (disclosed in JP Unexamin. Publn. No. 86-268664) with an alkylating agent, optionally; followed by acid amide formation, tetrazole formation, and/or salt formation. That is, the compounds (I) of this invention are prepared by reacting 2,6-di-tert-butyl-4-mercaptophenol of the formula (II):

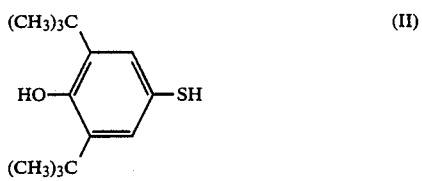

with an alkylating agent, optionally followed by acid amide formation, or tetrazole formation. If necessary, the compounds (I) of this invention may be subjected to salt formation to give their pharmaceutically acceptable salts.

Each reaction is described in more detail as follows.

① R is —CN:

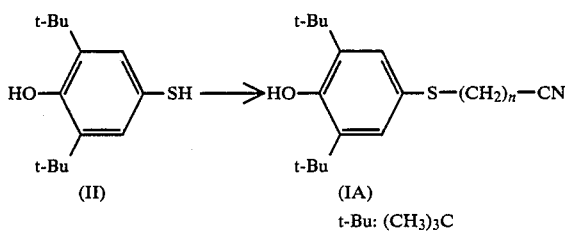

In the reaction scheme above, n is an integer of from 2 to 6.

This reaction is to prepare the nitriles (IA) of this invention.

This reaction may be carried out using halogenoalkanonitrile as an alkylating agent in a conventional procedure for sulfide synthesis.

As the halogenoalkanonitrile used in this reaction, 3-bromopropionitrile, 4-bromobutylonitrile, 5-bromopentancarbonitrile, 6-bromohexancarbonitrile, and the like are exemplified.

The reaction may be carried out in the presence of a base (e.g., sodium hydroxide, potassium hydroxide, calcium hydroxide, calcium carbonate, pyridine, triethylamine, tetrabutylammonium hydroxide, or the like) in a solvent such as alcohol (e.g., methanol, ethanol, propanol, tert-butanol, or the like), ether (e.g., diethyl ether, tetrahydrofuran, or the like), halogenated hydrocarbon (e.g., chloroform, dichloromethane, or the like), or N,N-dimethylacetamide at cooling to room temperature or under reflux for a period of about 10 minutes to several ten hours. In case that water-immiscible solvents such as halogenated hydrocarbon (e.g., dichloromethane, chloromethane, dichloroethane, or the like) or aromatic hydrocarbon (e.g., benzene or the like) are used, the reaction may be carried out in a heterogeneous phase of an organic layer and an aqueous layer in the presence of a phase transfer catalyst (e.g., hexadecyl-tri-n-butylphosphonium bromide) for acceleration of the reaction.

② R is 5-1H-tetrazolyl and/or its tautomer 5-2H-tetrazolyl:

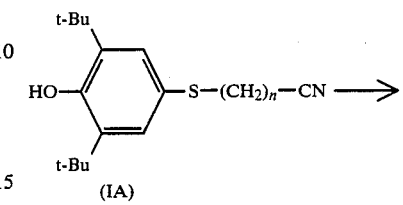

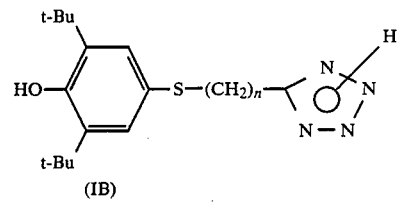

In the reaction scheme above, n is an integer of from 2 to 6.

The tetrazole (IB) can be prepared from the compound (IA) of this invention.

The reaction is performed in a conventional manner disclosed in A. Nohara et al., J. Med. Chem., 22, 290, 1979; W. G. Finnegan et al., J. Am. Chem. Soc., 80, 3908, (1958); E. P. Vacek et al., Synthesis, 1133, (1987); and the like. That is to say, the reaction may be carried out using an azide salt such as ammonium azide, sodium azide, lithium azide, aluminum azide, or the like, in a solvent such as 1-methyl-2-pyrrolidone, dimethylformamide, diethylsulfoxide, ether (e.g., diethyl ether, tetrahydrofuran) or the like, if necessary, in the presence of a phase-transfer catalyst such as triethylammonium chloride, ammonium chloride, tetramethylammonium chloride, or the like under heating for a period of several hours.

The salt of tetrazole (IB) can be prepared in a conventional manner, for example, by reacting the tetrazole (IB) in a solvent with a theoretical amount of a suitable base such as an alkali metal or alkaline earth metal hydroxide or carbonate, ammonium hydroxide, ammonia, or an organic amine. The salt can be isolated by freeze-dry or by filtration if it is sufficiently insoluble in the solvent.

③ R is carbamoyl:

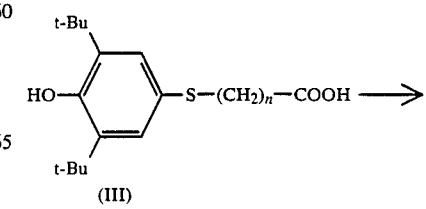

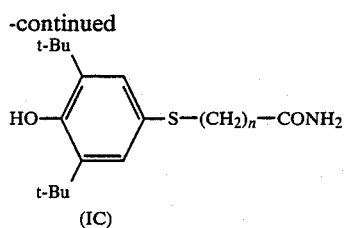

(IC)

In the reaction scheme above, n is an integer of from 2 to 6.

In this step, the carboxylic acids (III) are converted into the acid amides (IC) of this invention.

This step can be achieved by (a) an acid anhydride method, (b) an acid halide method, or (c) an active ester method.

In the acid anhydride method, an acid anhydride of carboxylic acid (III), or usually in a form of a mixed acid anhydride of carboxylic acid (III) is treated with ammonia. The mixed acid anhydride is prepared by reacting the carboxylic acid (III) in the presence of an organic base (e.g., triethylamine, pyridine) with monoalkyl chloroformate (e.g., ethyl chloroformate, isobutyl chloroformate, or the like) in a solvent such as chlorinated hydrocarbon (e.g., chloroform, dichloromethane, dichloroethane, or the like) at a temperature of $-20°$ C. to $40°$ C. The mixed acid anhydride can be prepared by treatment of the carboxylic acid with trifluoroacetic anhydride in the same manner as mentioned above. Thus the prepared mixed acid anhydride is treated with a conc. aqueous ammonia or ammonia gas in a water-miscible solvent such as ether (e.g., dioxane, tetrahydrofuran) or ketone (e.g., acetone) at $0°$ C. to $50°$ C. optionally under pressure to give the acid amide (IC).

In an acid halide method, the acid halide which prepared by treating the carboxylic acid (III) with thionyl chloride or phosgen in the presence of an organic base or treating the powdered alkali salt of carboxylic acid (III) with oxalyl chloride in a solvent such as chlorinated hydrocarbon (e.g., chloroform, dichloromethane, dichloroethane) is treated with conc. aqueous ammonia or ammonia gas in the same manner as mentioned above to give the acid amide (IC).

In the active ester method, the acid amide can be directly prepared from the carboxylic acid (III) by treating with an aqueous ammonia in the presence of a condensing agent such as dicyclohexylcarbodiimide (DCC). The active ester of carboxylic acid (III) can be converted into the acid amide (IC) by reacting with an aqueous ammonium or ammonia gas in a water-miscible solvent such as ether (e.g., dioxane, tetrahydrofuran, or the like), alcohol (e.g., methanol, ethanol, or the like), ketone (e.g., acetone) or the like at room temperature.

The carboxylic acid (III) can be prepared by reacting the compound represented by the formula (II) with an alkylating agent according to a known synthetic method for a sulfide.

As the alkylating agent, halogenated fatty acid such as an haloalkanoic acid (e.g., 2-bromoethanoic acid, 3-bromopentanoic acid, 4-bromohexanoic acid, or the like) is exemplified.

The compounds (I) of this invention can strongly inhibit the incorporation of LDL into macrophages, the oxidation of lipid, the formation of ulcer, and/or action of lipoxygenase. Therefore, they are useful for prevention and treatment of arteriosclerosis, gastric ulcer, allergic diseases, rheumatoid arthritis, myocardial ischemia, cataract, liver injury, cerebral cell disturbance, diabetes mellitus, thyroid function disorder, or inflammatory disease, phlegmonous symptoms, or the like.

The compounds (I) of this invention can be administered orally; or parenterally to patients. For the oral administration, they are normally formulated into conventional preparation form such as solid preparations (e.g., tablets, powders, capsules, granyles) or liquid preparations (e.g., aqueous dispersion, oily suspension, syrups, elixirs). For the parenteral administration, they are usually applied via injectable form, such as that of aqueous solutions or oily dispersions. On the formulation of the above preparations, there may be used excipients, binding agent, lubricants, solvents, solubilizers, emulsifiers, dispersants, and the like. Other additives such as preservatives and stabilizing agents may be also used.

The dosage of the compounds (I) of this invention varies with the dosage form, age, bodyweight, symptom of the patient, or the like but usually ranges from about 5 to 1000 mg per day, preferably, 20 mg to 200 mg per day for oval administration and 0.5 mg to 500 mg per day, preferably, 5 mg to 50 mg per day for parenteral administration.

Practical and presently preferred embodiments for this invention are shown in the following Examples, but it should be understood that these examples are given only for the illustrative purposes and do not limit the scope of the present invention thereto.

REFERENTIAL EXAMPLE 1

3-(3,5-Di-tert-butyl-4-hydroxy)phenythiopropanonitrile Ie

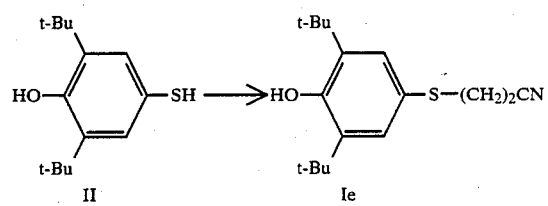

To a solution of 15 g of 2,6-di-tert-butyl-4-mercaptophenol II in 90 ml of ethanol was added 12.6 ml (1 eq.) of 5N-sodium hydroxide in a nitrogen atmosphere under ice-cooling. The mixture was stirred at the same temperature for 5 minutes and 5.22 ml (1 eq.) of 3-bromopropionitrile was added thereto and the resultant mixture was stirred for 1 hour at room temperature. The reaction mixture was poured into water and extracted with ethyl acetate. The organic layer was washed with water, dried over magnesium sulfate and concentrated under reduced pressure. The residue was recrystallized with ethyl ether-n-hexane to give 14.63 g of the aimed product as first crop (mp. 94.5°–95° C.). The mother liquour was crystallized to give 3.00 of the aimed product as second crop (mp. 94°–95° C.) Yield 96.1%.

Anal. Calcd. (%) $C_{17}H_{25}NOS=291.44$: C, 70.05; H, 8.65: N, 4.81; S, 11.00; Found (%): C, 70,07; H, 8.65; N, 4.81; S, 11.01.

IR$\nu$max(CHCl$_3$) cm$^{-1}$: 3640, 2250, 1154.

NMR $\delta$ppm (CDCl$_3$): 1.22(s, 18H), 2.56(t, J=7.6 Hz, 2H), 3.00 (t,J=7.6 Hz, 2H), 5.35(s, 1H), 7.30 (s, 2H).

EXAMPLES 1 to 4

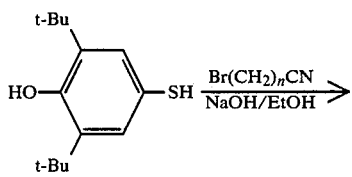

TABLE 1

| Ex. No. | n | S.M. A (weight) | Ethanol B (ml) | 5N—NaOH C (ml) | D (weight) |
| --- | --- | --- | --- | --- | --- |
| 1 | 3 | 15 g | 90 | 12.6 | 9.3 g |
| 2 | 4 | 15 g | 90 | 12.6 | 10.2 g |
| 3 | 5 | 5 g | 30 | 4.2 | 3.7 g |
| 4 | 6 | 15 g | 90 | 12.6 | 12.0 g |

S.M.: Starting Material

TABLE 2

| Ex. No. | Compd. No. | n | E(Weight) | mp. or bp. | Yield (%) | $^1$H-NMR δppm (CDCl$_3$) | IR νmax(CHCl$_3$) | Analysis Calcd. (%) Found (%) |
| --- | --- | --- | --- | --- | --- | --- | --- | --- |
| 1 | I$^a$ | 3 | 17.85 g | mp. 72~73° C. | 92.9 | 1.43(s, 18H), 1.93(t, t, J=7Hz, 2H), 2.52(t, J=7Hz, 2H), 2.93(t, J=7Hz, 2H), 5.27(s, 1H), 7.27(s, 2H) | 3640 2250 1155 | C, 70.77; H, 8.91; n, 4.59 S, 10.50 C, 70.83; H, 9.15; N, 4.78 S, 10.40 |
| 2 | I$^b$ | 4 | 16.30 g | mp. 57~58° C. | 81.1 | 1.43(s, 18H), 1.70~1.90 (m, 4H), 2.36(t, J=6.6Hz, 2H), 2.85(t, J=6.6Hz, 2H), 5.24(s, 1H), 7.24(s, 2H) | 3640 2250 1156 | C, 71.42; H, 9.15; N, 4.38 S, 10.04 C, 71.31; H, 9.12; N, 4.47 S, 9.85 |
| 3 | I$^c$ | 5 | 1st crop 5.31 g 2nd crop 0.23 g | mp. 55~57° C. mp. 45~48° C. | 79.3 | 1.41(s, 18H), 1.48~1.72(m, 6H), 2.31(t, J=6.8Hz, 2H), 2.81(t, J=6.8Hz, 2H), 5.19(s, 1H), 7.21(s, 2H) | 3640 2245 1155 | C, 72.02; H, 9.37; N, 4.20 S, 9.61 C, 72.17; H, 9.42; N, 4.18 S, 9.48 |
| 4 | I$^d$ | 6 | 21 g | bp. 210° C. (1 mmHg) (oil) | 96.0 | 1.40~1.70(m, 26H), 2.33 (t, J=7Hz, 2H), 2.83(t, J=7Hz, 2H), 5.20(s, 1H), 7.23(s, 2H) | 3640 2245 1155 | C, 72.57; H, 9.57; N, 4.03 S, 9.23 C, 72.36; H, 9.56; N, 4.15 S, 9.17 |

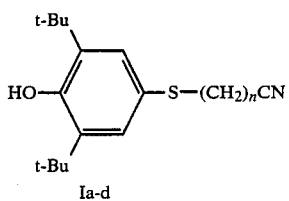

Ia-d (General Procedure)

To a solution of A (weight) of 2,6-di-tert-butyl-4-mercaptophenol in B (ml) of ethanol was added C (ml) of 5N sodium hydroxide while cooling with ice in a nitrogen atmosphere. The resultant mixture was kept at the same temperature for 5 minutes, D (weight) of bromoalkanonitrile was added thereto, and the mixture was stirred for 1 hour at room temperature. The reaction mixture was poured into water and extracted with ethyl acetate. The organic layer was washed with water, dried over magnesium sulfate, and concentrated under reduced pressure. The residue was chromatographed on silica gel. The fractions eluted with n-hexane ethyl acetate (10:1 to 4:1) were collected and concentrated under reduced pressure. The residue was recrystallized from ethyl ether - n-hexane to give E (weight) of the aimed product. According to the above general procedure, the following compounds were obtained.

The reaction conditions are shown in Table 1 and physical constants in Table 2.

4-(3,5-Di-tert-butyl-4-hydroxy)phenylthiobutylonitrile Ia, 5-(3,5-Di-tert-butyl-4-hydroxy)phenylthiopentanonitrile Ib, 6-(3,5-Di-tert-butyl-4-hydroxy)phenylthiohexanonitrile Ic, and 7-(3,5-Di-tert-butyl-4-hydroxy)phenylthioheptanonitrile Id.

EXAMPLE 5

5-[2-(3,5-Di-tert-butyl-4-hydroxy)phenylthioethyl]-tetrazole Ie

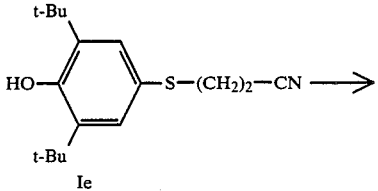

Ie

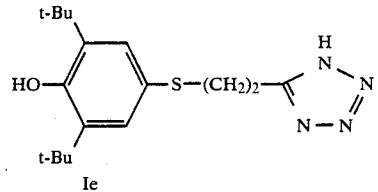

Ie

To a solution of 10.0 g of 3-(3,5-di-tert-butyl-4-hydroxy)phenylthiopropanonitrile Ie in 300 ml of 1-methyl-2-pyrrolidinone were added 7.3 g of triethylamine hydrochloride and 6.7 g of sodium azide and the mixture was heated at 150° C. overnight under stirring. The reaction mixture was poured into water and extracted with ethyl acetate. The organic layer was washed with water, dried over magnesium sulfate, and concentrated under reduced pressure. The residue was chromatographed on silica gel and the fractions eluted with ethyl acetate were collected and recrystallized from ethyl acetate - toluene to give 2.7 g of the aimed product Ie in 23.5% yield. mp. 187° to 188° C.

Anal. Calcd. (%) $C_{17}H_{26}N_4OS$=334.48: C, 61.04; H, 7.84; N, 16.75; S, 9.59; Found (%): C, 61.22; H, 7.76; N, 16.63; S, 9.56.

IRνmax(Nujol) cm$^{-1}$: 3605, 3115, 1554, 1248, 1236.

NMR δppm (CD$_3$OD): 1.38(s, 18H), 3.17(s, 4H), 7.18(s, 2H).

EXAMPLES 6 to 9

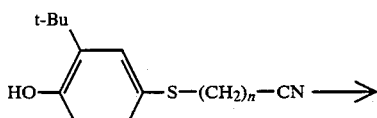

TABLE 3

| Ex. No. | n | S.M. A (weight) | 1-methyl-2-pyrrolidinone B (ml) | NEt$_3$·HCl C (weight) | NaN$_3$ D (weight) |
|---|---|---|---|---|---|
| 6 | 3 | 10.0 g | 300 | 6.9 g | 6.4 g |
| 7 | 4 | 5.0 g | 150 | 3.3 g | 3.1 g |
| 8 | 5 | 4.4 g | 137 | 2.8 g | 2.6 g |
| 9 | 6 | 5.0 g | 150 | 3.0 g | 2.8 g |

TABLE 4

| Ex. No. | Compd. Ia-d No. | n | E (weight) | Mp. (°C.) | Yd. (%) | $^1$H-NMR δppm (CD$_3$OD) | IR νmax | Analysis Calcd. (%) Found (%) |
|---|---|---|---|---|---|---|---|---|
| 6 | If | 3 | 1st Crop 7.35 g 2nd Crop 0.82 g | 154~155 149~151 | 71.6 | 1.37(s, 18H), 1.99(t, t J=7.5Hz, 2H), 2.83(t, J=6.9 Hz, 2H), 3.07(t, J=7.5Hz, 2H), 7.18(s, 2H) | Nujol 3600, 3130 1559, 1250 1236, 1133 | C$_{18}$H$_{28}$N$_4$OS C, 62.03; H, 8.10; N, 16.08; S, 9.20 C, 62.20; H, 8.13; N, 15.89; S, 9.04 |
| 7 | Ig | 4 | 4.25 g | 123~124 | 74.9 | 1.37(s, 18H), 1.50~1.70 (m, 2H), 1.80~1.85(m, 2H), 2.79(t, J=7.0Hz, 2H), 2.92 (t, J=7.5Hz, 2H), 7.17(s, 2H) | CHCl$_3$ 3640, 3425 3140, 1555 1154 | C$_{19}$H$_{30}$N$_4$OS·0.5C$_5$H$_6$ C, 65.79; H, 8.28; N, 13.95; S, 7.98 C, 66.09; H, 8.25; N, 13.80; S, 7.80 |
| 8 | Ih | 5 | 2.75 g | 118~119 | 54.7 | 1.38(s, 18H), 1.40~1.68(m, 4H), 1.76(t, t J=7Hz, 2H), 2.77(t, J=7Hz, 2H), 2.91(t, J=7Hz, 2H), 7.17(s, 2H) | CHCl$_3$ 3640, 3425 3140, 1555 1153 | C$_{20}$H$_{32}$N$_4$OS C, 63.79; H, 8.57; N, 14.88; S, 8.52 C, 63.86; H, 8.50; N, 14.84; S, 8.39 |
| 9 | Ii | 6 | 2.57 g | 45~46 | 45.7 | 1.23~1.88(m, 24H), 1.74 (t, t J=7.0Hz, 2H), 2.75(t, J×6.5Hz, 2H), 2.90(t, J=7.6 Hz, 2H), 7.17(s, 2H) | CHCl$_3$ 3640, 3420 J=1603 1554, 1153 | C$_{21}$H$_{34}$N$_4$OS·0.3C$_6$H$_6$ C, 66.14; H, 8.72; N, 13.53; S, 7.75 C, 66.44; H, 8.54; N, 13.90; S, 7.41 |

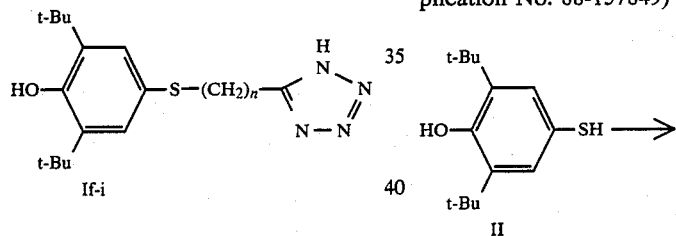

If-i (General Procedure)

To a solution of A (weight) of 3-(3,5-di-tert-butyl-4-hydroxy)phenylthiopropanonitrile Ie in B (ml) of 1-methyl-2-pyrrolidinone were added C (weight) of triethylamine hydrochloride and D (weight) of sodium azide and the mixture was heated at 150° C. overnight under stirring. The reaction mixture was poured into water and extracted with ethyl acetate. The organic layer was washed with water, dried over magnesium sulfate, and concentrated under reduced pressure. If required, the residue was chromatographed on silica gel and the fractions eluted with ethyl acetate were collected and recrystallized from benzene - n-hexane to give E (weight) of the aimed product.

According to the above general procedure, the reaction was conducted under the conditions as shown in Table 3 to give the products as shown below and in Table 4.

5-[3-(3,5-Di-tert-butyl-4-hydroxy)phenylthiopropyl]-tetrazole If,

5-[4-(3,5-Di-tert-butyl-4-hydroxy)phenylthiobutyl]-tetrazole Ig,

5-[5-(3,5-Di-tert-butyl-4-hydroxy)phenylthiopentyl]-tetrazole Ih, and

5-[6-(3,5-Di-tert-butyl-4-hydroxy)phenylthiohexyl]-tetrazole Ii.

REFERENTIAL EXAMPLE 2

Preparation of 6-(3,5-di-tert-butyl-4-hydroxy)phenylthiohexanoic acid III (Compound disclosed in JP. Application No. 88-157849)

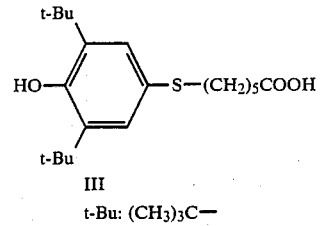

t-Bu: (CH$_3$)$_3$C—

To a solution of 2.0 g of 2,6-di-tert-butyl-4-mercaptophenol II in 18 ml of ethanol was added 3.36 ml of 5N sodium hydroxide in a nitrogen atmosphere while being cooled with ice. The resultant mixture was kept at the same temperature for 5 minutes, 1.63 g of 5-bromopentanoic acid was added thereto. The mixture was stirred for 1 hour and then allowed to stand at room temperature overnight. The reaction mixture was poured into water and acidified with 2N hydrochloric acid in the presence of ethyl acetate. The mixture was extracted with ethyl acetate and the organic layer was washed with water, dried over magnesium sulfate, and concentrated under reduced pressure to give oily residue, which was chromatographed on silica gel. The fractions eluted with toluene - ethyl acetate (9:1 to 2:1) were collected and recrystallized from ethyl ether - n-hexane to give 1.75 g (first crop, mp. 57°–57.5° C.) and then 400 mg (second crop, mp. 57°–57.5° C.) from the mother liquour. Yield 72.7%.

EXAMPLE 10

6-(3,5-Di-tert-butyl-4-hydroxy)phenylthiohexanamide Ij

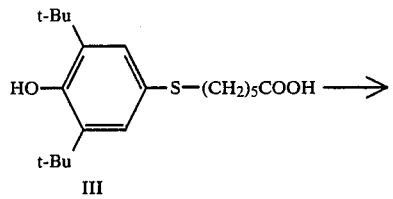

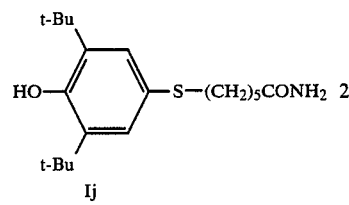

To a solution of 2.0 g of 6-(3,5-di-tert-butyl-4-hydroxy)phenylthiohexanoic acid III in 40 ml of chloroform were added 1.58 ml of triethylamine and then 0.65 ml of ethyl chloroformate in a nitrogen atmosphere under ice-cooling. The resultant mixture was stirred at 25° to 40° C. for 4 hours and then ammonia gas was slowly introduced under ice-cooling. The reaction mixture was concentrated under reduced pressure to give a crystalline residue, which was then washed with water. The residue was dissolved in ethyl acetate and applied on silica gel column. The fractions eluted with ethyl acetate were collected and recrystallized from ethyl acetate - n-hexane to give 1.58 g of the aimed product Ij in 79.3% yield. Mp. 138° to 141° C.

Anal. Calcd. (%) for $C_{20}H_{33}NO_2S \cdot 0.2H_2O$: C, 67.64; H, 9.48; N, 3.94; S, 9.03; Found (%): C, 67.82; H, 9.43; N, 3.64; S, 9.10.

IR$\nu$max(Nujol) cm$^{-1}$: 3560, 3445, 3305, 3240, 3200, 1730, 1650, 1614, 1133, NMR $\delta$ppm(d-DMSO): 1.30~1.60(m, 24H), 2.00 (t, J=7 Hz, 2H), 2.80(t, J=7 Hz, 2H), 6.67(br, s, 2H), 7.02(s, 2H), 7.20 (br, s, 2H).

TEST EXAMPLE 1

Suppression on production of peroxidized lipid in a homogenate of rat brain:

SD strain rats (body weight, about 200 g) were sacrificed by cutting down their heads, and the brains were taken out. The brains were homogenated with a 4-fold amount of 0.05M phosphate-sodium chloride buffer (pH 7.4) and centrifuged at 1000×g for 10 minutes. The supernatant was kept at −80° C. for storage.

The supernatant was diluted with a 2-fold amount of the same phosphate - sodium chloride buffer as above, and 0.48 ml of the dilution was combined with 30 μl of ethanol per se (vehicle) or ethanol solution containing a test compound (final concentration: 0.01 mM), followed by incubation at 37° C. for 30 minutes. The reaction was terminated by addition of 0.01% butylhydroxytoluene (BHT) in ethanol (20 μl) and 25% metaphosphoric acid (125 μl) and subjected to elimination of proteins. The peroxidized lipid in the supernatant was measured by the thiobarbituric acid (TBA) method according to the description in Ohkawa et al.: Anal. Biochem., vol. 95, page 351 (1979). The amount of peroxidized lipid produced was compared with that in the vehicle applied group and expressed in % control. The results are shown in Table 5.

TABLE 5

| Test Compound Number* | Peroxidized Lipid Produced (Expressed in % to Control) (Final Concentration: 0.01 mM) |
|---|---|
| Ia | 4.5 |
| Ib | 3.6 |
| Ic | 9.2 |
| Id | 5.4 |
| Ie | 8.1 |
| If | 5.7 |
| Ig | 4.1 |
| Ih | 9.5 |
| Ii | 4.4 |
| Ij | 4.7 |
| Probucol | 58.3 |

*Test compound numbers correspond to those in the examples.

TEST EXAMPLE 2

Effect against hydrochloric acid ethanol-induced gastric ulcer.

To male JCD-SD rats (weight: 220–275 g) which have been fasted for 24 hours was administered orally 1 ml of 150 mM hydrochloric acid - 60% ethanol. After an hour, the stomachs were excised. The ulcer size as determined by measuring the length of each lesion under stereoscopic microscope and the sum of individual lesion length is expressed as lesion index. The vehicle (1% to 10% ethanol) and the test compounds were administered orally 30 minutes before the hydrochloric acid -ethanol administration. The percent suppression was calculated from the lesion indexes of treated versus untreated animals. The results are shown in Table 6.

TABLE 6

| Test Compd. Number* | Inhibitory Rate (Expressed in % to Control) | |
|---|---|---|
| Ia | 94.3 ± 14.8 | |
| Ib | 61.2 ± 18.4 | |
| Ic | 19.2 ± 8.4 | $p < 0.01$ |
| Id | 77.3 ± 16.8 | |
| Ie | 37.2 ± 5.9 | $p < 0.001$ |
| If | 52.1 ± 20.0 | |
| Ig | 49.2 ± 13.0 | $p < 0.05$ |
| Ih | 52.5 ± 16.6 | |
| Ii | 46.6 ± 13.4 | $p < 0.05$ |
| Ij | 70.8 ± 8.5 | |
| Probucol | 75.4 ± 22.1 | |

*Test compounds numbers are identical to the numbers in the examples.

It is understood from the above results, the compounds of this invention show an excellent anti-oxidation activity to lipids. And they also prevent the incorporation of denatured LDL (due to oxidized by $Cu^{2+}$ and smoking) into macrophages.

The compounds of this invention can be expected to inhibit the formation of atheroma in the itial stage of arteriosclerosis. Thus, they would be useful as antisclerosis drugs.

We claim:

1. A compound of the formula:

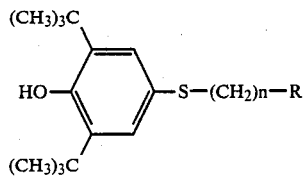

wherein R is cyano, carbamoyl, or 5-tetrazolyl; n is an integer of 2 to 6; provided that when R is cyano, n is not 2; or a pharmaceutically acceptable salt thereof.

2. A pharmaceutical composition for use in the treatment of arteriosclerosis of mammals comprising a pharmacologically effective amount of at least one compound of the formula:

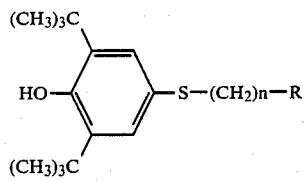

wherein R is cyano, carbamoyl, or 5-tetrazolyl; n is an integer of 2 to 6; provided that when R is cyano, n is not 2, or a pharmaceutically acceptable salt thereof.

* * * * *